( 12 ) United States Patent
Liao et al.

(10) Patent No.: US 12,263,583 B2
(45) Date of Patent: Apr. 1, 2025

(54) COUNTERBALANCE MECHANISM INCLUDING DRIVE RATIO

(71) Applicant: Intuitive Surgical Operations, Inc., Sunnyvale, CA (US)

(72) Inventors: Hsien-Hsin Liao, Sunnyvale, CA (US); Timothy P. Haines, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/420,599

(22) Filed: Jan. 23, 2024

(65) Prior Publication Data

US 2024/0157585 A1    May 16, 2024

Related U.S. Application Data

(62) Division of application No. 17/501,060, filed on Oct. 14, 2021, now Pat. No. 11,919,153.

(Continued)

(51) Int. Cl.
| | |
|---|---|
| *B25J 19/00* | (2006.01) |
| *A61B 34/00* | (2016.01) |
| *B25J 9/10* | (2006.01) |

(52) U.S. Cl.
CPC ............ *B25J 19/002* (2013.01); *A61B 34/71* (2016.02); *B25J 9/1045* (2013.01); *B25J 19/0016* (2013.01); *A61B 2034/715* (2016.02)

(58) Field of Classification Search
CPC ..... B25J 19/002; B25J 19/0016; A61B 34/71; A61B 2034/715; F16H 2019/0609; F16H 2019/0695
See application file for complete search history.

(56) References Cited

U.S. PATENT DOCUMENTS

| | | |
|---|---|---|
| 6,378,829 B1 | 4/2002 | Strater et al. |
| 7,837,674 B2 | 11/2010 | Cooper |
| (Continued) | | |

FOREIGN PATENT DOCUMENTS

| | | | | |
|---|---|---|---|---|
| DE | 202009014646 U1 | * | 4/2011 | ............ F16H 19/06 |

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Bobby Rushing, Jr.
(74) *Attorney, Agent, or Firm* — IP Spring

(57) ABSTRACT

Implementations relate to a counterbalance mechanism including a force transformation mechanism that provides a drive ratio. In some implementations, a counterbalance apparatus includes a spring, a first tension element, a second tension element, a force transformation mechanism coupled to the spring by the first tension element and coupled to the second tension element, and a plurality of counterbalance pulleys coupled to the second tension element. At least one of the counterbalance pulleys is coupled to a load that is moveable with reference to a mechanical ground, and a force provided by the spring is modified in magnitude by the force transformation mechanism and is applied to the load via the second tension element. The force transformation mechanism includes a plurality of elements and the modification of the force is based on a drive ratio of the elements of the force transformation mechanism.

20 Claims, 5 Drawing Sheets

Related U.S. Application Data

(60) Provisional application No. 63/092,355, filed on Oct. 15, 2020.

(56) References Cited

U.S. PATENT DOCUMENTS

| | | | |
|---|---|---|---|
| 8,220,765 B2 | 7/2012 | Bailey | |
| 8,490,953 B2 | 7/2013 | Luke et al. | |
| 9,050,119 B2 | 6/2015 | Devengenzo et al. | |
| 9,301,807 B2 | 4/2016 | Duval | |
| 9,850,994 B2 | 12/2017 | Schena | |
| 9,856,688 B2 * | 1/2018 | Elie | E05F 15/627 |
| 9,877,792 B2 | 1/2018 | Cooper | |
| 10,271,913 B2 * | 4/2019 | Yoshii | A61B 34/30 |
| 2018/0200008 A1 | 7/2018 | Cooper | |
| 2020/0121478 A1 | 4/2020 | Woge et al. | |
| 2021/0322127 A1 | 10/2021 | Martin et al. | |
| 2022/0118633 A1 | 4/2022 | Liao et al. | |

* cited by examiner

COUNTERBALANCE MECHANISM INCLUDING DRIVE RATIO

The present application is a divisional of U.S. patent application Ser. No. 17/501,060, filed Oct. 14, 2021 and titled "Counterbalance Mechanism Including Driving Ratio," which claims priority to U.S. Provisional Patent Application No. 63/092,355, filed Oct. 15, 2020 and titled "Counterbalance Mechanism Including Gear Ratio," the entire contents of both of which are hereby incorporated by reference.

BACKGROUND

Load positioning systems can be used in a variety of applications. In some examples, a load includes one or more links of a mechanical linkage such as a mechanical arm. For example, a grip can be connected to a mechanical arm and can be moved by a user in one or more degrees of freedom provided by the mechanical arm to provide input to a system. One or more of the links and/or the grip can be considered a load of the mechanical arm.

In some systems, forces can be applied to a mechanical arm by motors. For example, the grip may be included in a control input device that can be manipulated by a user to control functions of a system, and the motors can provide force feedback to the control input device and/or can position the mechanical arm in a particular workspace. For example, control input devices can be used in teleoperated surgical devices that allow the user to control various types of manipulator instruments at a surgical site to perform surgical procedures. Some systems can also make use of control input devices to allow a user to control one or more functions or devices. In other examples, load positioning systems can be provided at a controlled manipulator device of a teleoperated system, e.g., at mechanical arms of the manipulator device used to hold and move various instruments or other tools. Motors at the manipulator device move the mechanical arms to controlled positions and orientations at a worksite. Load positioning systems are also used in other types of systems and devices.

A load positioning system operating on earth is subject to gravitational force. When the revolute axes of a mechanical arm are not parallel to the direction of gravitational force, the gravitational force needs to be countered by actuators, such as motors. Such actuators consume energy even when the mechanical arm is stationary.

A counterbalance mechanism is commonly employed in load positioning systems to apply force to a mechanical arm or other load to balance the load, e.g., compensate for the effects of gravity on the load. Counterbalance mechanisms often include passive elements such as springs. In systems using actuators such as motors, this reduces the requirements on the energy consumption and the force output capability of the actuators. For example, a counterbalance mechanism provides gravity compensation when the motors are not powered, and allows forces of lower magnitude to be output by motors applying forces to the mechanical arm since, in the presence of the counterbalance mechanism, the motors need not provide as much counterbalance force to compensate for gravity.

As a revolute joint of a mechanical arm rotates, the effect of gravity on the joint does not stay constant and is typically periodic in nature. To balance this periodic gravitational torque about a revolute joint, a counterbalance mechanism commonly incorporates a set of pulleys, cable, and spring. As the joint rotates, the counterbalance mechanism produces a periodic torque that reduces or cancels the gravity torque. To achieve this, a conventional counterbalance mechanism relies on matching particular design parameters to the gravity load. However, factors such as packaging constraints and discrete spring selections may make it difficult to obtain a viable counterbalance mechanism for particular systems and applications.

SUMMARY

Implementations of the present application relate to counterbalance mechanisms including a force transformation mechanism that, for example, provides a drive ratio. In some implementations, a counterbalance apparatus includes a spring, a first tension element, a second tension element, a force transformation mechanism coupled to the spring by the first tension element and coupled to the second tension element, and a plurality of counterbalance pulleys coupled to the second tension element. At least one of the counterbalance pulleys is coupled to a load that is moveable with reference to a mechanical ground, and a force provided by the spring is modified in magnitude by the force transformation mechanism and is applied to the load via the second tension element. The force transformation mechanism includes a plurality of elements and the modification of the force is based on a drive ratio of the elements of the force transformation mechanism.

Various implementations and examples of the counterbalance apparatus are described. In some implementations, the drive ratio is based on a relative size of the elements of the force transmission mechanism, and the force of the spring is modified by the force transformation mechanism such that a gravity force on the load is balanced. In some examples, the drive ratio is selected based on a particular spring rate, and a magnitude of the force provided by the spring to the load is configured based at least on the particular spring rate and drive ratio. The drive ratio can be selected based on a specified extension length of the spring, and a travel distance of the spring during operation of the counterbalance mechanism is configured based at least on the specified extension length of the spring and the drive ratio. In various implementations, the modification of the forces is a force reduction or is a force amplification.

In some implementations, the elements of the force transformation mechanism include a first transform pulley having a first radius and a second transform pulley having a second radius, the first and second transform pulleys being rigidly coupled together, wherein the first radius is greater than the second radius. In some examples, the first tension element can be coupled to the first transform pulley and the second tension element can be coupled to the second transform pulley, or in other examples, the first tension element is coupled to the second transform pulley and the second tension element is coupled to the first transform pulley. In various implementations, the force transformation mechanism can include a belt and pulley mechanism, a plurality of spur gears, or a capstan drive mechanism. In some example implementations, the first tension element and second tension element are cables.

In some implementations, at least one of the counterbalance pulleys is coupled to a load, the load includes a first member, a second member, and a rotary joint having a rotary joint axis, the first member is rotationally coupled to the second members at the rotary joint and are rotatable with respect to each other about a rotary joint axis of the rotary joint, the second member is coupled to a mechanical ground, and the force transformation mechanism is rotationally coupled to the mechanical ground. In some implementations, the plurality of counterbalance pulleys includes a first counterbalance pulley and a second counterbalance pulley having a rotary axis, the first counterbalance pulley rotationally coupled to the first member of the load at the rotary joint and rotatable about the joint axis, and the second counterbalance pulley rotationally coupled to the first member of the load and rotatable about the rotary axis of the second counterbalance pulley, wherein the rotary axis of the second counterbalance pulley is different than the rotary joint axis and this rotary axis is in line, along a length of the first member, with the rotary joint axis and with a center of mass of the first member. In some examples, the counterbalance apparatus further includes a counterbalance element coupled to a mechanical ground, the second tension element includes a first end portion coupled to the force transformation mechanism, and the second tension element includes a second end portion coupled to the counterbalance element. In various examples, the counterbalance element can be a pulley coupled to the mechanical ground and having a center axis different than the rotary joint axis and rotary axis of the second counterbalance pulley, or can be a cylindrical segment rotationally coupled to the force transformation mechanism and rigidly coupled to the mechanical ground.

In some implementations, the plurality of counterbalance pulleys includes a first counterbalance pulley and a second counterbalance pulley, the counterbalance apparatus includes a counterbalance element, the second tension element includes a first end portion coupled to the force transformation mechanism, the second tension element includes a second end portion coupled to the counterbalance element, and the second tension element is at least partially wrapped around the first and second counterbalance pulleys and counterbalance element. In some examples, at least one of the counterbalance pulleys is coupled to a load, the spring has a spring constant, a first distance is defined between an axis of rotation of the first counterbalance pulley and an axis of rotation of the second counterbalance pulley, a second distance is defined between the axis of rotation of the first counterbalance pulley and a center axis of the counterbalance element, a drive ratio is based on a plurality of elements of the force transformation mechanism that modify a force provided by the spring to the load via the second tension element, and the first counterbalance pulley, the second counterbalance pulley, the force transformation mechanism, and the spring are configured such that a product that is based on the first distance, the second distance, the spring constant, and the drive ratio is matched to the load to counterbalance the load against a gravitational force. In some implementations, the counterbalance apparatus is embodied in a user control system of a teleoperated surgical system, or a manipulator device of a teleoperated surgical system.

In some implementations, an apparatus includes a mechanical arm including a rotary joint, a first member, and a second member rotationally coupled to the first member at the rotary joint. A spring is coupled to the second member, a first tension element is coupled to the spring, and a force transformation mechanism is coupled to the second member and to the first tension element. A second tension element is coupled to the force transformation mechanism, and a plurality of counterbalance pulleys are coupled to the mechanical arm, wherein at least one of the counterbalance pulleys is coupled to the first member. The second tension element is wrapped at least partially around at least one of the counterbalance pulleys. The force transformation mechanism includes elements having a drive ratio, and is configured to mechanically transform a force provided by the spring and transmitted via the second tension element to the first member, wherein the mechanical transformation of the forces is based on the drive ratio of the elements of the force transformation mechanism.

Various implementations and examples of the apparatus are described. For example, in some implementations, the force provided by the spring is modified by the force transformation mechanism such that a gravity force on the second member of the mechanical arm is balanced. In some implementations, the drive ratio determines the mechanical transformation to be a force reduction or a force amplification based on a relative size of the elements of the force transformation mechanism.

In some implementations, the elements of the force transformation mechanism include a first element having a first radius and a second element having a second radius, and the drive ratio is based on a ratio between the first radius and the second radius. In some implementations, the first tension element is coupled to the first element and the second tension element is coupled to the second element. In some examples, the first element is a first transform pulley and the second element is a second transform pulley, wherein the first transform pulley and the second transform pulley have the same axis of rotation and the first transform pulley is rigidly coupled to the second transform pulley. In some implementations, the force transformation mechanism includes a belt and pulley mechanism, a plurality of spur gears, or a capstan drive mechanism.

In some implementations, the drive ratio is selected based on a particular spring rate or extension length of the spring, a magnitude of the force provided by the spring to the load is configured based at least on the particular spring rate and drive ratio, and a travel distance of the spring during operation of the counterbalance mechanism is configured based at least on the extension length of the spring and the drive ratio. In some implementations, the force transformation mechanism is rotationally coupled to a mechanical ground, the second member of the mechanical arm is coupled to the mechanical ground, and the counterbalance pulleys include a first counterbalance pulley and a second counterbalance pulley, the first counterbalance pulley coupled to the mechanical arm at the rotary joint of the mechanical arm, the second counterbalance pulley coupled to the second member of the mechanical arm, the rotary joint of the mechanical arm has an axis of rotation, and the first counterbalance pulley having an axis of rotation aligned with the axis of rotation of the rotary joint. In some examples, the apparatus further includes a counterbalance element rotationally coupled to the force transformation mechanism and rigidly coupled to the mechanical ground, the second tension element includes a first end portion coupled to the force transformation mechanism, and the second tension element includes a second end portion coupled to the counterbalance element.

In some implementations, an apparatus includes means for providing a spring force and transforming means for mechanically transforming the spring force to a transformed force. The apparatus includes means for transmitting the spring force to the transforming means, and means for rotationally redirecting the transformed force to a load. The apparatus includes means for transmitting the transformed force from the transforming means to the means for rotationally redirecting the transformed force. The transformed force counterbalances a gravity force on the load. In various implementations and examples of the apparatus, the transforming means reduces or amplifies the spring force to provide the transformed force. In some implementations, the transforming means mechanically transforms the spring force by applying a drive ratio to the spring force. In some implementations, the transforming means includes first rotating means having a first radius and second rotating means having a different radius.

DETAILED DESCRIPTION

Figure 1:
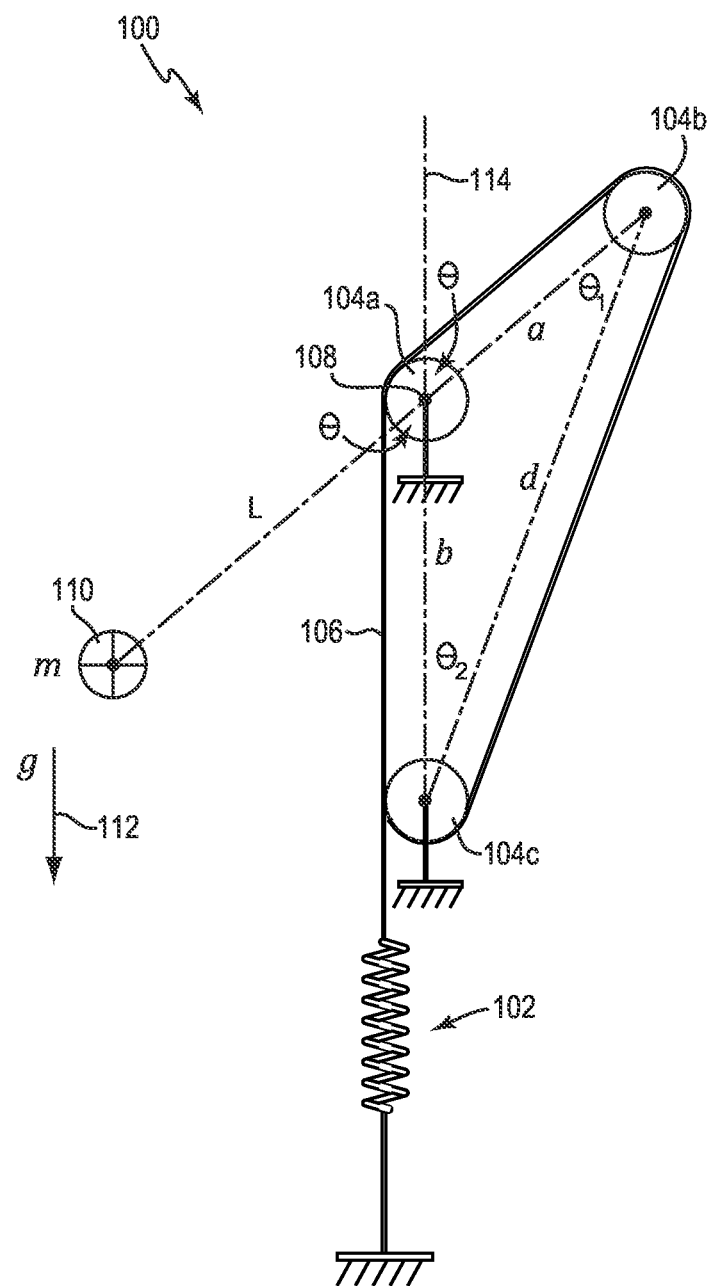
FIG. 1 is a diagrammatic illustration of an example conventional counterbalance mechanism.

Implementations described herein relate to counterbalance mechanisms including a force transformation mechanism that provides, e.g., a drive ratio. In described implementations, a counterbalance apparatus balances a load against gravitational forces. The load can be moveable, e.g., rotatable, with reference to a mechanical ground. The counterbalance apparatus includes a spring and a force transformation mechanism coupled to the spring by a first tension element, such as a first cable. A second tension element, such as a second cable, is coupled to the force transformation mechanism and is wrapped at least partially around multiple counterbalance pulleys, one or more of which are coupled to the load.

Forces provided by the spring are mechanically transformed (e.g., modified) by the force transformation mechanism and, after the transformation, applied to the load via the second tension element. The mechanical transformation provides mechanical advantage to the spring force, which can be force reduction or force amplification, and can be based on a drive ratio of elements of the force transformation mechanism. For example, the drive ratio can be based on a size of the elements with reference to each other and can be selected to cause the forces of the spring to balance a gravity force on the load. In some examples, the elements are two transform pulleys rigidly coupled to each other and rotationally coupled to a mechanical ground. For example, the drive ratio can be based on a ratio of the radius of the first transform pulley to the radius of the second transform pulley. In some examples, the first tension element can be coupled to one of the transform pulleys and the second tension element can be coupled to the other of the transform pulleys. In some implementations, the force transformation mechanism can include other types of mechanisms, e.g., a belt and pulley mechanism, a plurality of spur gears, or a capstan drive mechanism.

Various additional features of the counterbalance mechanism are disclosed. In some examples, the load can be a first member rotationally coupled to a grounded second member at a rotary joint having a joint axis, e.g., forming a mechanical arm. In some implementations, the counterbalance pulleys include a first pulley rotationally coupled to the first member at the rotary joint, and a second pulley rotationally coupled to the first member and rotatable about a different rotary axis. In various implementations, a counterbalance element, such as a cylindrical pulley or cylindrical segment, can be coupled to the second tension element and coupled to the mechanical ground. The tension element can be at least partially wrapped around the first pulley, the second pulley, and the counterbalance element.

Described features provide a counterbalance mechanism that balances a load against gravity to be implemented with increased flexibility in design parameters for different applications. For example, features include a drive ratio of a force transformation mechanism provided between a spring and pulley system that introduces an additional design parameter for the counterbalance mechanism in addition to parameters such as spring rate (k) and distances between counterbalance pulleys and element. The drive ratio can be selected to gear up or down the force provided by a spring depending on the application and/or other selected components of the counterbalance mechanism.

For example, changing the drive ratio increases or decreases the spring constant needed for the spring to balance the load. In some examples, if a stiffer spring (higher spring rate) is used in the counterbalance mechanism, a gear-down force transformation mechanism can be provided to reduce the magnitude of spring force on the load, thus allowing the stiffer spring to be used. If a softer spring (lower spring rate) is used in the mechanism, a gear-up force transformation mechanism can be provided to increase the magnitude of spring force on the load, thus allowing the softer spring to be used. The gearing up or down can be easily implemented by selecting the size of the elements (e.g., pulleys or gears) of the force transformation mechanism.

In another example, the drive ratio can be selected to increase or decrease the required amount of distance that the spring travels (e.g., extension length of the spring) in operation of the counterbalance mechanism. In some examples, if only a small distance is available in a housing for the spring in the counterbalance mechanism, a gear-up force transformation mechanism can be provided to increase the magnitude of spring force on the load and allow a spring having a lower spring rate and smaller extension length to be used. Changing the drive ratio thus can change (e.g., reduce) package size for components of the counterbalance mechanism, as needed.

Parameters such as the drive ratio allow a wider range of options in design to accommodate a counterbalance mechanism to a desired application, e.g., by widening the spring selection range and relaxing packaging constraints for the counterbalance mechanism. For example, this design parameter flexibility allows a counterbalance mechanism to be tailored to specific packaging constraints of a mechanical system. In further examples, procurement of components for the counterbalance mechanism is easier since the flexibility widens the range of springs that are suitable for the mechanism.

The counterbalance implementations described herein can be used in a variety of types of devices. In some examples, a described counterbalance apparatus can be coupled to a mechanical linkage, e.g., a mechanical arm, that includes a handle or grip that is grasped by a user during operation. For example, the handle and mechanical arm may be included in or coupled to a control input device that can be manipulated by a user to control functions of a system. Motors or other actuators output force on the mechanical arm and/or can position the mechanical arm in a particular workspace. A counterbalance apparatus described herein can be coupled to the mechanical arm and provide counterbalance force to the mechanical arm and/or handle. In some examples, the control input device can be included or embodied in a user control system (e.g., console) of a teleoperated surgical system that allows the user to control manipulator arms and surgical instruments of a manipulator device located at a surgical site to perform surgical procedures. In some systems, the control input device can control any of various other functions or devices.

In other examples, any of the counterbalance implementations described herein can be included or embodied in a manipulator device of a teleoperated system that is controlled by a user control system. For example, in a teleoperated surgical system, the manipulator device can include one or more mechanical arms that hold any of various surgical instruments or other tools, and which can perform surgical procedures at a surgical site. Motors at the manipulator device move the mechanical arms, based on commands from the user control system, to positions and orientations at the surgical site. A counterbalance apparatus described herein can be coupled to the manipulator arm and provide counterbalance force to the manipulator arm and/or surgical instrument. The counterbalance apparatus described herein can alternatively be used in other types of systems and devices.

The term "drive ratio" as used herein refers to a ratio of rotation of one rotating element to rotation of a coupled rotating element, and can be specified based on radiuses of the rotating elements, number gear teeth of the rotating elements, etc. As used herein, a drive ratio can apply to any of various types of drive mechanisms, e.g., pulleys connected by a belt, sprockets connected by a chain, interlocking gears, etc.

The terms "center," "parallel," "perpendicular," "orthogonal," "aligned," or particular measurements in degrees, Hertz, or other units as used herein need not be exact and can include typical engineering tolerances. As referred to herein, a mechanically grounded member is kinematically coupled to a mechanical ground (e.g., mechanically connected to ground directly or indirectly). As used herein, the term "proximal" refers to an element that is close to (or closer to) a mechanical ground and the term "distal" refers to an element that is away from (or further from) a mechanical ground. The term "torque" as used herein refers to rotational forces and/or refers to a context of rotational motion, and in various implementations using one or more described features, other types of forces can be used as appropriate in place of or in addition to torque, e.g., linear forces or other forces, and/or forces in a context of translational motion.

FIG. 1 is a diagrammatic illustration of an example conventional counterbalance mechanism 100. Counterbalance mechanism 100 includes a counterbalance spring 102 and counterbalance pulleys 104a, 104b, and 104c (collectively referred to as pulleys 104). A tension element 106 is coupled to spring 102 and wraps around pulleys 104.

Spring 102 is coupled to a mechanical ground at one end and is coupled to tension element 106 at its other end. Spring 102 provides a spring force on tension element 106. Spring 102 has a spring constant k.

Tension element 106 is routed from one end at spring 102 around pulleys 104a, 104b, and 104c, and terminates at pulley 104c, where the tension element is anchored at its other end. Pulley 104c is fixed to the mechanical ground, e.g., a grounded member of a mechanical arm. Pulley 104a is rotationally coupled to a member, which in this example can be a rotatable link of the mechanical arm, and has an axis of rotation 108 that is coaxial with a joint axis of the rotatable link of the mechanical arm. Pulley 104b is rotationally coupled to the link of the mechanical arm and swings about axis 108 and pulley 104a with the link as it rotates. The link has a mass m and a center of mass 110 that is on the opposite side of axis 108 from the pulley 104b. Pulley 104b is positioned in line with center of mass 110 and the axis of rotation 108.

In operation, the rotatable link having center of mass m can rotate about axis 108. Spring 102 provides a force on tension element 106 which resists motion of pulley 104b about the axis 108, thus providing a counterbalance force on the rotatable link that opposes the gravitational force 112 on the rotatable link (e.g., if the counter balance mechanism is detached from the rotatable link, mass 110 would come to a rest at the 6 o'clock position about axis 108).

Parameters of the counterbalance mechanism include distances between components. The planar distance between axis of rotation 108 and the axis of rotation of pulley 104b is a. The planar distance between axis of rotation 108 and the center axis of pulley 104c is b. The distance between the center axis of pulley 104c and axis of rotation of pulley 104b is d, which is a function of the selected parameters a and b and additionally, the angle θ. The planar distance of the center of mass 110 to the axis of rotation 108 is L, which is a parameter of the counterbalance mechanism as a "lever arm" length of the load of the mechanism. A different link may have a different mass 110 and/or different lever arm length L. The counter balance design parameters k, a, and b are chosen to balance the gravity load for the given link having a particular mass 110 and lever arm length L.

As shown in FIG. 1, an angle θ is denoted between the current orientation of pulley 104b and an orientation of pulley 104b that would cause the three pulleys 104a, 104b, and 104c to be aligned, e.g., their centers intersected by a single line. In FIG. 1, the three-pulley-aligned orientation is along the vertical line 114. This same angle θ is between center of mass 110 and its stable equilibrium position along vertical line 114.

At any given angle θ, the mass m of the link generates a moment, $M_{grav}$, about the rotary axis 108, as indicated in Equation 1:

$$M_{grav} = m \cdot g \cdot L \sin(\theta 0) \tag{1}$$

where g is the gravitational acceleration.

If the tension element 106 is chosen such that the spring deflection of spring 102 is equal to the distance a+b when θ is zero, the moment generated by the counterbalance mechanism, $M_{cb}$, about the rotary axis 108 is as shown in Equation 2:

$$M_{cb} = -k \cdot a \cdot b \cdot \sin(\theta) \tag{2}$$

where k is the spring constant of spring 102.

As the link rotates, the counterbalance mechanism produces a periodic torque that cancels the gravity torque. To achieve this, the counterbalance mechanism relies on matching the product of three design parameters to the gravity load. The three design parameters are k, a, and b. As a result, by exactly matching the product of k, a, and b with the parameter product of m, g, and L, the counterbalance mechanism can perfectly balance the gravity load of the rotatable link.

Figure 2:
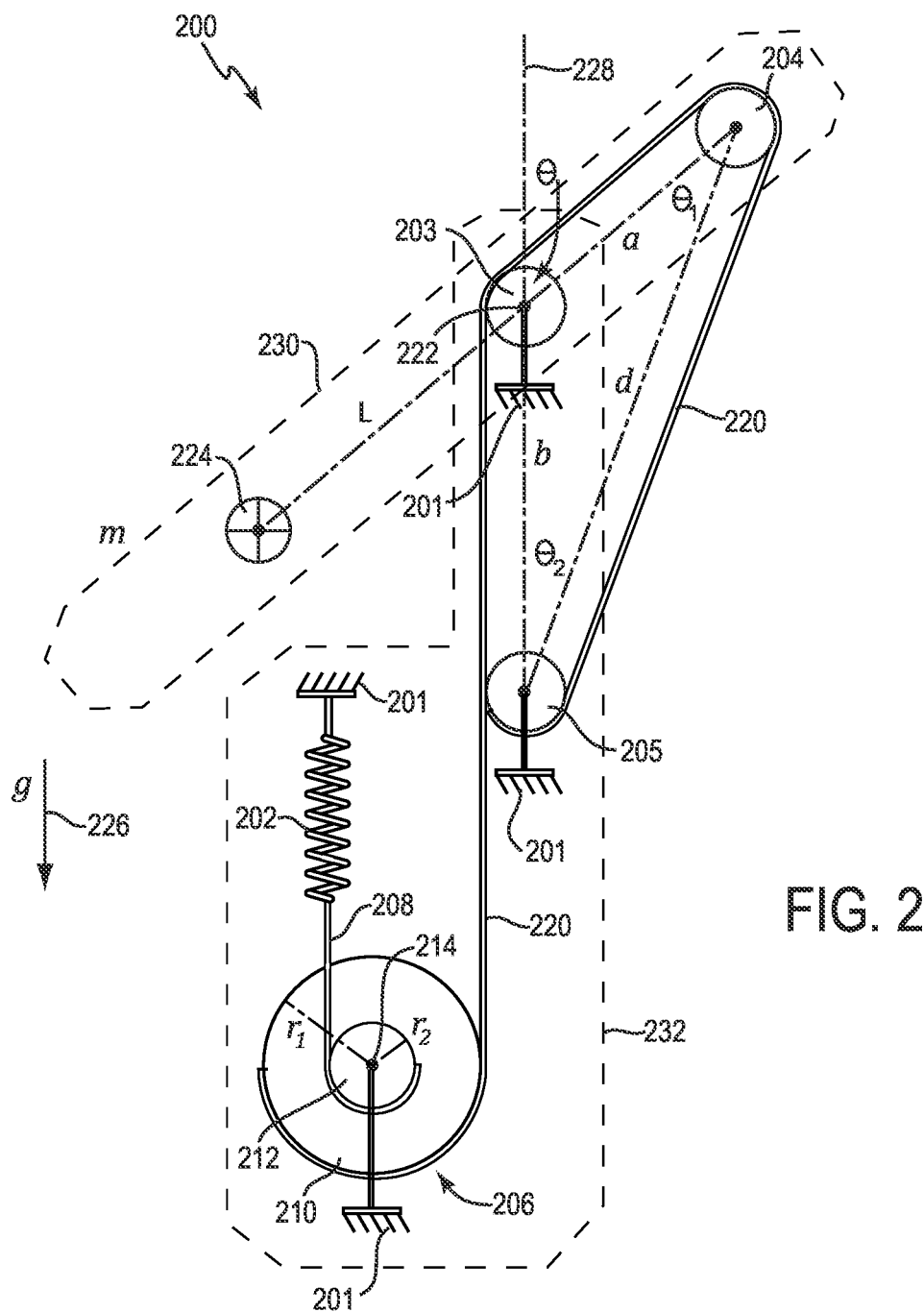
FIG. 2 is a diagrammatic illustration of an example counterbalance mechanism including one or more features of the present disclosure, according to some implementations.

FIG. 2 is a diagrammatic illustration of an example counterbalance mechanism 200 including one or more features of the present disclosure, according to some implementations. Counterbalance mechanism 200 can be used to provide counterbalance forces to a load, e.g., a load such as a rotating member of a mechanical arm, to counter (e.g., cancel or reduce) gravitational forces on the load. The sizes and lengths of components, and distances between components, shown in FIG. 2 and the other figures herein are not actual dimensions, but rather schematic examples shown for simplicity. Portions shown in dashed lines are representations of components that are part of a system to which the counterbalance mechanism 200 is connected.

Counterbalance mechanism 200 is coupled to a load that is counter balanced against gravity. In this example, the load includes a rotatable member 230, indicated by dashed lines in FIG. 2. Rotatable member 230 can have a variety of different dimensions, shapes, etc. In some examples, as shown, rotatable member 230 is coupled by a rotary joint to a grounded member 232, indicated by dashed lines in FIG. 2. Rotatable member 230 is rotatable about axis 222 with reference to grounded member 232. Grounded member 232 can be a mechanical ground 201 with respect to the counterbalance mechanism 200. Grounded member 232 can have a variety of different dimensions, shapes, etc. In some implementations, counterbalance mechanism 200 is provided between rotatable member 230 and grounded member 232.

In some implementations, rotatable member 230 and grounded member 232 are included in a mechanical arm, e.g., as links in the linkage of a mechanical arm. In some implementations, grounded member 232 can be coupled to another member, e.g., another link of the mechanical arm. In some example implementations, the mechanical arm can be used in a user control system, e.g., the arm can be coupled to a control input device that can be manipulated by a user in one or more degrees of freedom. In some example implementations, the mechanical arm can be used as a manipulator arm in a manipulator device or slave device operating at a worksite, and movement of the manipulator arm is controlled by a user that is correspondingly manipulating a control input device associated with the manipulator arm. In various other implementations, the mechanical arm is used in other applications.

Counterbalance mechanism 200 includes a counterbalance spring 202, counterbalance pulleys 203 and 204, counterbalance element 205, and force transformation mechanism 206.

Spring 202 is coupled to mechanical ground 201 at a first end of the spring. A second end of spring 202 is coupled to a first end of a tension element 208. Spring 202 provides a spring force on tension element 208. Spring 202 can be used as a tension spring, as shown, or alternatively as a compression spring in which, for example, tension element 208 is coupled to the first end of the spring and passes through the spring, such that a load causes the spring to be compressed.

Tension element 208, and any of the other tension elements described in the various implementations herein, can be any flexible element that can be routed to and contacts (e.g., wraps at least partially around) the components of the counterbalance mechanisms described herein. For example, one or more tension elements can be a flexible tension element, e.g., a steel tension element. In some implementations, the tension elements are cables. In some implementations, one or more of the tension elements can be belt, chains, or other flexible elements. The tension elements described herein transmit force from one component to another, e.g., from a spring to a force transformation mechanism, or from a force transformation mechanism to a load (e.g., to counterbalance pulley(s) of the load).

In the implementation of FIG. 2, force transformation mechanism 206 modifies the magnitudes of forces provided by spring 202. Force transformation mechanism 206 includes a first transform pulley 210 and a second transform pulley 212. Both first transform pulley 210 and second transform pulley 212 rotate about rotational axis 214. In some examples, first transform pulley 210 can be rotationally coupled to mechanical ground 201. In some examples, first transform pulley 210 can be rotationally coupled directly to a mechanical ground, can be rotationally coupled to a grounded member 232 (e.g., link) of a mechanical arm, or can be coupled to another member of the mechanical arm that is grounded with respect to counterbalance mechanism 200.

Second transform pulley 212 can be rigidly coupled to first transform pulley 210 such that both first transform pulley 210 and second transform pulley 212 rotate in unison about axis 214. In some examples, force transformation mechanism 206 can be manufactured as multiple separate parts (e.g., separate first transform pulley 210 and second transform pulley 212) that are assembled to form force transformation mechanism 206, or mechanism 206 can be manufactured as a single, unitary part that includes pulleys 210 and 212 (e.g., machined from a single piece of material). In some implementations, second transform pulley 212 can be rotationally coupled to mechanical ground 201 in a similar manner that first transform pulley 210 is coupled to ground as described above, e.g., second transform pulley 212 can be rotationally coupled to ground instead of first transform pulley 210 being coupled to ground.

A second end of tension element 208 is coupled to second transform pulley 212. For example, tension element 208 wraps at least partially around and terminates at second transform pulley 212, where tension element 208 is anchored at its second end. In the example shown, tension element 208 is wrapped in a first direction (e.g., clockwise as shown in FIG. 2) around second transform pulley 212 from the second end of tension element 208. In various implementations, tension element 208 can be wrapped around second transform pulley 212 by a different amount depending on the implementation, e.g., depending on a range of motion of rotating member 230.

A tension element 220 is coupled to first transform pulley 210 at a first end of tension element 220, and this first end is anchored at first transform pulley 210. Tension element 220 wraps at least partially around first transform pulley 210. In the example shown, tension element 220 is wrapped in a second direction (e.g., counterclockwise as shown in FIG. 2) around first transform pulley 210 from the first end of tension element 220, and the second direction is opposite to the first direction of tension element 208 around pulley 212. In various implementations, tension element 220 can be wrapped around first transform pulley 210 by a different amount depending on the implementation, e.g., depending on the range of motion of rotating member 230.

First transform pulley 210 and second transform pulley 212 rotate about axis 214 in unison and in the same direction due to their rigid coupling. Thus, in one example, if force on tension element 220 causes first transform pulley 210 to rotate about axis 214 in a counterclockwise direction in the viewpoint of FIG. 2, second transform pulley 212 also rotates in the same direction, thus pulling tension member 208 and causing the length of spring 202 to increase (extend or stretch) in this example. Similarly, rotation of second transform pulley 212 in a clockwise direction caused by spring 202 and tension element 208 causes rotation of first transform pulley 210 in the same direction, which causes pulling force on tension element 220 toward the force transformation mechanism 206.

Tension element 220 is routed from its first end at first transform pulley 210 toward a counterbalance pulley system and wraps at least partially around pulleys 203 and 204 and counterbalance element 205. Tension element 220 terminates at counterbalance element 205 where tension element 220 is anchored at its second end (e.g., at an opposite end to the first end of the tension element 220). In various implementations, tension element 220 can be wrapped around element 205 by a different amount depending on the implementation, e.g., depending on the range of motion of rotating member 230.

In some examples, from its first end at first transform pulley 210, tension element 220 wraps partially around counterbalance element 205. Counterbalance element 205 is fixed to a mechanical ground 201, e.g., rigidly coupled to grounded member 232. In some implementations, counterbalance element 205 can be a pulley (e.g., cylinder) that has the same radius as counterbalance pulleys 203 and 204 and has a center axis that is different than an axis of rotation of the first pulley 203 and an axis of rotation of the second pulley 204. In some implementations, counterbalance element 205 is rigidly coupled to the same ground member 232 to which force transformation mechanism 206 is rotationally coupled. In some implementations, counterbalance element 205 and force transformation mechanism 206 can be coupled to different ground members. In some implementations, counterbalance element 205 is not cylindrical and has a different shape, or is an element that is a feature or portion of grounded member 232. For example, element 205 can be a feature on the grounded member 232 that that has a curved surface that is a portion of a cylinder and that has the same radius as pulleys 203 and 204. An example of another implementation of element 205 is shown with respect to FIG. 3.

Pulley 203 can be rotationally coupled to rotatable member 230 and has an axis of rotation 222 that is coaxial with a joint axis of the rotary joint that couples the rotatable member 230 to the grounded member 232. Pulley 204 is rotationally coupled to rotatable member 230 and swings about axis 222 and pulley 203 with the rotatable member 230 as it rotates. Rotatable member 230 has mass m and a center of mass 224 that can be on the opposite side of axis 222 from pulley 204. In some implementations, pulley 204 is positioned in line, along a length of the rotatable member 230, with center of mass 224 and axis of rotation 222.

In some implementations, one or more of the pulleys of the counterbalance mechanism 200 (or of any of the counterbalance mechanisms described herein) can include grooves on their circumferential surface to support a tension element, e.g., to cause an engaged tension element to be securely wrapped, to stay in place around the pulley, and/or to prevent the tension element from drifting toward an edge of the pulley during pulley rotation.

In operation, rotatable member 230 can rotate about axis 222. Spring 202 and tension elements 208 and 220 provide a counterbalance force on rotatable member 230 in opposition to the force of gravity 226 being exerted on the rotatable member 230. For example, spring 202 provides a force on tension element 208 which resists swing motion of pulley 204 about the axis 222 caused by rotation of rotatable member 230, thus providing a counterbalance force on rotatable member 230 that opposes gravitational force on the rotatable member. In some example implementations, this application of counterbalance forces allows reduced force magnitudes to be output from actuators (e.g., motors) to move or support the rotatable member 230 against gravity as compared to implementations that do not provide such counterbalance forces.

As shown in FIG. 2, an angle θ is denoted between the current orientation of pulley 204 and an orientation of the pulley 204 that would cause the pulleys 203 and 204 and element 205 to be aligned, e.g., their centers intersected by a single line. In FIG. 2, the aligned orientation is along the vertical line 228. This same angle θ exists between the center of mass 224 and its stable equilibrium position along vertical line 228.

Design parameters of the counterbalance mechanism 200 include distances between components of the mechanism 200 and/or rotatable member 230. One design parameter is a, the planar distance between axis of rotation 222 and the axis of rotation of pulley 204. Another design parameter is b, the planar distance between axis of rotation 222 and the center axis of element 205. The distance between the center axis of element 205 and the axis of rotation of pulley 204 is d, which is a function of the selected parameters a and b and the angle θ. For example, since pulley 204 rotates with rotatable member 230, distance d varies and is a function of a, b, and angle θ at which the rotatable member is currently oriented.

Another design parameter of the counterbalance mechanism 200 is k, the spring rate (e.g., spring constant or stiffness) of spring 202. The planar distance of center of mass 224 to axis of rotation 222 is L, which is a parameter of the counterbalance mechanism as a "lever arm" length of the load of the mechanism (rotatable member 230). A different rotatable member 230 may have a different center of mass 224 and/or different lever arm length L. The counterbalance design parameters k, a, and b can be chosen to balance the gravity load for the given rotatable member 230 having a particular center of mass 224 and lever arm length L.

Balancing the gravity load of the rotatable member 230 can be performed by matching the product of the three parameters k, a, and b to the gravity load, similarly as explained above for FIG. 1 and equations (1) and (2). As rotating member 230 rotates, the counterbalance force applied to the rotating member is dynamically adjusted to compensate for gravity as applied during the rotation.

Counterbalance mechanism 200 allows more design flexibility relative to conventional implementations (such as in FIG. 1) by enabling variable parameter values of components of force transformation mechanism 206 provided between tension element 220 and spring 202. Force transformation mechanism 206 provides a mechanical transformation (e.g., force modification providing mechanical advantage) between the loop of tension element 220 and spring 202. For example, the mechanical transformation can be a force reduction or a force amplification.

The amount of mechanical transformation is based on a drive ratio between first transform pulley 210 and second transform pulley 212. The mechanical transformation is obtained by providing first transform pulley 210 with a radius r1 and second transform pulley 212 with a radius r2 that is different than the radius r1. For example, the drive ratio between first transform pulley 210 and second transform pulley 212 can be R=r1/r2. This gearing type of effect (e.g., gear ratio) can alternatively be achieved with other force transformation mechanisms such as a spur gear set, planetary gear set, capstan drive, etc., some examples of which are described below with respect to FIGS. 5 and 6.

To use counterbalance mechanism 200 in a conventional manner as described with reference to FIG. 1, radius r1 is set equal to radius r2 such that R=1, thus applying no mechanical transformation to the spring force provided by spring 202.

A particular amount of mechanical transformation can be applied to the counterbalance force provided by spring 202 to tension element 220 and rotating member 230 by making the radius of one of the transform pulleys 210 or 212 different than the radius of the other transform pulley 212 or 210, e.g., by setting the drive ratio R be different than 1. For example, to obtain a force amplification (e.g., gear up) implementation, the drive ratio R can be made less than 1 (R<1), and tension element 220 sees greater force than tension element 208, such that the spring force from spring 202 is amplified on tension element 220 compared to the implementation in which R is equal to 1. Using a drive ratio R<1 and all other components staying the same, the travel of spring 202 is greater than in the implementation in which R is equal to 1.

Conversely, to obtain a force reduction (e.g., gear reduction or gear down) implementation, the drive ratio R can be made greater than 1 (R>1), and tension element 220 sees lower force than tension element 208, such that the spring force from spring 202 is reduced on tension element 220 compared to the implementation in which R is equal to 1. Using a drive ratio R>1 and all other components staying the same, the travel of spring 202 is less than in the implementation in which R is equal to 1.

For example, the counterbalance mechanism 200 shown in FIG. 2 provides force reduction, where R>1.

The moment generated by the counterbalance mechanism 200 on rotating member 230 about axis 222 is shown in Equation 3:

$$M_{cb} = \frac{-k \cdot a \cdot b \cdot \sin(\theta)}{R^2} \quad (3)$$

To match the gravity load of rotating member 230, the counterbalance mechanism 200 can be designed to satisfy the relationship shown in Equation 4:

$$\frac{k \cdot a \cdot b}{R^2} = m \cdot g \cdot L \quad (4)$$

When θ is zero, the spring deflection of spring 202 depends on the particular mechanical advantage (e.g., drive ratio) that has been selected for force transformation mechanism 206. Specifically, when θ is zero, the spring deflection is as shown in Equation 5:

$$\frac{a+b}{R} \quad (5)$$

A different magnitude of force is applied to tension element 220 or tension element 208 at force transformation mechanism 206 depending on the drive ratio used, which causes a different amount of spring travel in spring 202 based on the drive ratio. Thus, a drive ratio can be selected based on a particular spring rate of a spring 202 that is being used, or a particular spring rate of spring 202 can be selected based on the drive ratio being used. For example, a geardown force transformation mechanism 206 can be selected to allow use of a stiffer spring than a conventional design given the same pulley system arrangement (higher k, but same a and b). Conversely, a gear-up force transformation mechanism 206 can be selected to allow use of a softer spring (lower k, same a and b). Furthermore, the design can accommodate a spring having a specified extension length by selecting a particular drive ratio, since the extension length of the spring is associated with a particular spring rate of the spring and changing one of these parameters changes the other parameter. For example, the specified extension length of the spring can be a maximum or minimum extension length as constrained by the particular implementation, e.g., based on available space for the spring in a housing.

The extra design capability and flexibility in counterbalance mechanism 200 is advantageous. For example, springs that are available (e.g., through vendors) to include in a counterbalance design may have only particular or a limited number of distinct spring rates (k). Counterbalance mechanism 200 allows an available spring to be used that may not have the precise spring rate needed, by selecting the drive ratio of the force transformation mechanism 206 to allow a different spring rate to provide the counterbalance force in the mechanical system. Component procurement thus is easier since the flexibility widens the range of springs that are suitable for counterbalance mechanism 200.

Furthermore, some applications or uses of a mechanical arm or other mechanism may have unique packaging constraints, which may limit the other parameters of the counterbalance mechanism, e.g., the extension length (e.g., deflection) of spring 202 and/or the physical distances (e.g., a and/or b) allowed between counterbalance pulleys 203 and 204 and between counterbalance pulley 203 and counterbalance element 205, respectively. Counterbalance mechanism 200 allows parameters such as spring extension length and distances between pulleys to be adjusted to accommodate physical constraints, by configuring force transformation mechanism 206 with a selected drive ratio to compensate for particular physical lengths while enabling the required counterbalance forces to be provided for a particular implementation.

Thus, for example, the additional design parameter enabled via the drive ratio of force transformation mechanism 206 can allow counterbalance mechanism 200 to be configured appropriately to constraints of a particular system (e.g., component, packaging, etc.) and/or application.

In some examples, implementing a counterbalance mechanism for a mechanical system in accordance with one or more features described herein can include determining the parameter values for a counterbalance mechanism to balance a load of a mechanical system of a particular application against gravitational forces. In some example implementations, parameters of components of counterbalance mechanism, other than the force transformation mechanism 206, can be determined, including a spring and/or distances between the pulleys of the counterbalance pulley system. A drive ratio of force transformation mechanism 206 can then be selected to provide a counterbalance force to a rotatable member of the mechanical system. The drive ratio is selected based on the determined parameters of the components of the counterbalance mechanism and using the relationships shown in Equations (3), (4), and (5). For example, the spring constant k of the selected spring and the distance between the pulleys of the counterbalance pulley system are used to determine a drive ratio that provides the counterbalance force. The drive ratio is implemented by selecting elements for the force transformation mechanism that provide the drive ratio, e.g., by selecting two transform pulleys or gears with size, radii, or number of gear teeth that provide the drive ratio as described herein.

In other example implementations, a drive ratio of force transformation mechanism 206 can be first determined for the counterbalance mechanism. One or more additional parameters of counterbalance mechanism 200 (e.g., the spring rate, distances between counterbalance pulleys, etc.) can be selected based on the determined drive ratio using the relationships shown in Equations (3), (4), and (5). For example, the selected drive ratio is used to determine the spring constant k of the spring and/or the distance(s) between the counterbalance pulleys to provide the counterbalance force.

The counterbalance mechanism is implemented by placing the pulleys 203 and 204 and element 205 of the counterbalance pulley system at the selected distances from each other, routing tension element 208 from the selected spring 202 to the force transformation mechanism 206 having the selected drive ratio, and routing tension element 220 from the force transformation mechanism to the pulleys 203 and 204 and element 205 of the counterbalance pulley system coupled to rotatable member (passing the tension element over the pulleys as indicated in FIG. 2).

During operation of the counterbalance mechanism to balance a load, counterbalance force is applied to the load, e.g., a rotating member of a mechanical system such as a mechanical arm, and the counterbalance force is the spring force that has been reduced or amplified using the force transformation mechanism. The counterbalance force applied to the rotating member is adjusted based on the rotation and positions of the rotating member during operation, as described above.

Figure 3:
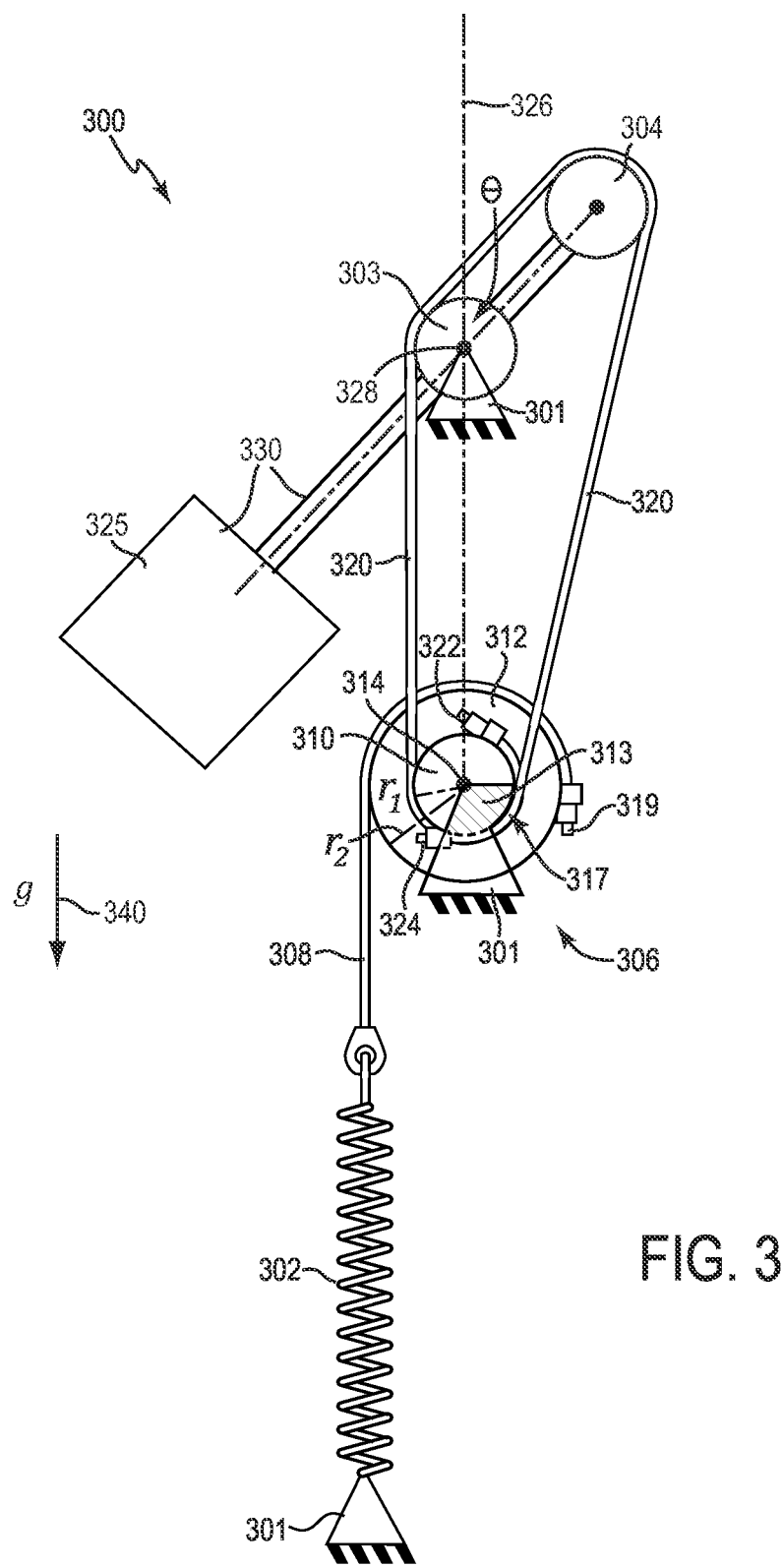
FIG. 3 is a diagrammatic illustration of another example counterbalance mechanism including one or more features of the present disclosure, according to some implementations.

FIG. 3 is a diagrammatic illustration of another example counterbalance mechanism 300 including one or more features of the present disclosure, according to some implementations. Counterbalance mechanism 300 can be used to provide counterbalance forces to a load, e.g., a rotating member of a mechanical arm, to counter gravitational forces on the load, similarly as counterbalance mechanism 200 described above for FIG. 2.

In this example, counterbalance mechanism 300 includes a spring 302, counterbalance pulleys 303 and 304, cylindrical segment 313, and force transformation mechanism 306.

Counterbalance mechanism 300 is coupled to a load that is counter balanced against gravity. In this example, the load includes a rotatable member 330. Rotatable member 330 can have a variety of different dimensions, shapes, etc. In some examples, as shown, rotatable member 330 is coupled by a rotary joint to a grounded member shown as mechanical ground 301 with respect to the counterbalance mechanism 300. In some implementations, the grounded member and can be similar to grounded member 232 of FIG. 2, and/or can have a variety of different dimensions, shapes, etc. Rotatable member 330 is rotatable about axis 328 with reference to ground 301. In some implementations, rotatable member 330 and the grounded member 301 are included in a mechanical arm, e.g., as links in the mechanical arm. In some implementations, the ground 301 can include or be coupled to another member, e.g., another link of the mechanical arm.

Spring 302 is coupled to mechanical ground 301 at a first end of the spring. A second end of spring 302 is coupled to a first end of a tension element 308. Spring 302 provides a spring force on tension element 308. Spring 302 can be used as a tension spring, as shown, or alternatively as a compression spring similarly as described for spring 202.

In the implementation of FIG. 3, force transformation mechanism 306 modifies the magnitudes of forces provided by spring 302. Force transformation mechanism 306 includes a first transform pulley 310 and a second transform pulley 312. First transform pulley 310 rotates about rotational axis 314 and can be rotationally coupled to mechanical ground 301. For example, first transform pulley 310 can be rotationally coupled directly to a mechanical ground, can be rotationally coupled to a grounded member of a mechanical arm that is coupled to mechanical ground, or can be coupled to another member of the mechanical arm that is grounded with respect to counterbalance mechanism 300.

Second transform pulley 312 rotates about the same rotational axis 314 as first transform pulley 310. Second transform pulley 312 can be rigidly coupled to first transform pulley 310 such that both first transform pulley 310 and second transform pulley 312 rotate in unison about axis 314. Second transform pulley 312 is also rotationally coupled to mechanical ground 301. In some examples, force transformation mechanism 306 can be manufactured as multiple separate parts (e.g., separate first transform pulley 310 and second transform pulley 312) that are assembled to form force transformation mechanism 306, or mechanism 306 can be manufactured as a single, unitary part that includes pulleys 310 and 312 (e.g., machined from a single piece of material).

In the example of FIG. 3, a second end of tension element 308 is coupled to second transform pulley 312. For example, tension element 308 wraps at least partially around and has a second end 319 that terminates (is anchored) at second transform pulley 312. In the example shown, tension element 308 is wrapped in a first direction (e.g., counterclockwise as shown in FIG. 3) around second transform pulley 312 from second end 319 of tension element 308. In various implementations, tension element 308 can be wrapped around second transform pulley 312 by a different amount depending on the implementation, e.g., depending on the range of motion of rotating member 330.

A tension element 320 is coupled to first transform pulley 310 at a first end 322 of tension element 320 (or a portion near the first end). An "end" of a tension member, as referred to herein, is a portion of the tension element that can be the actual end of the element (e.g., an end of a cable) or can be a portion of the tension element that connects to a component of the counterbalance mechanism. First end 322 is anchored at first transform pulley 310. Tension element 320 wraps at least partially around first transform pulley 310. In the example shown, tension element 320 is wrapped in a second direction (e.g., clockwise as shown in FIG. 3) around first transform pulley 310 from first end 322 of tension element 320, and the second direction is opposite to the first direction of tension element 308 around pulley 312. In various implementations, tension element 320 can be wrapped around first transform pulley 310 by a different amount depending on the implementation, e.g., depending on the range of motion of rotating member 330.

First transform pulley 310 and second transform pulley 312 rotate in unison about axis 314 in the same direction.

Thus, in one example, if force on tension element 320 causes first transform pulley 310 to rotate about axis 314 in a clockwise direction in the viewpoint of FIG. 3, second transform pulley 312 also rotates in the same direction, thus pulling tension element 308 and causing the length of spring 302 to increase (extend or stretch) in this example. Similarly, rotation of second transform pulley 312 in a counterclockwise direction (in the viewpoint of FIG. 3) caused by tension element 308 causes rotation of first transform pulley 310 in the same direction, which causes pulling force on tension element 320 toward the force transformation mechanism 306.

Tension element 320 is routed from its first end at first transform pulley 310 toward a counterbalance pulley system and wraps at least partially around pulleys 303 and 304. Tension element 320 terminates at a cylindrical segment 313 (or similar element) where tension element 320 is anchored at its second end 324 (or a portion near a second end).

Cylindrical segment 313 performs as a counterbalance element, e.g., similar to counterbalance element 205 of FIG. 2. Cylindrical segment 313 is rigidly coupled to mechanical ground 301 and can be rotationally coupled to first transform pulley 310 (as shown) and/or to second transform pulley 312. In this example, cylindrical segment 313 includes the hatched area shown in FIG. 3, which is rigidly coupled to mechanical ground 301. Cylindrical segment 313 includes a curved surface 317 which the tension element 320 contacts. In this example, a radius of curved surface 317 from axis 314 can be the same as the radius of the radius of the transform pulley to which it is rotationally coupled, e.g., radius r1 of first transform pulley 312 in this example. In some implementations, cylindrical segment 313 can be a round (cylindrical) pulley (e.g., of same radius as first transform pulley 310), a differently-sized segment of a cylinder (e.g., a segment having a curved surface with a different cross-sectional angle between its endpoints), or any element that includes a curved surface 317 against which the tension element 320 contacts. In some implementations, cylindrical segment 313 can be rigidly coupled to any member or feature that is mechanically grounded.

First transform pulley 310 and second transform pulley 312 rotate with respect to cylindrical segment 313. Cylindrical segment 313 can perform as a concentric pulley that anchors one end of the tension element 320, and can have a similar function to counterbalance element 205 shown in FIG. 2. An example of cylindrical segment 313 and force transformation mechanism 306 are described in greater detail below with respect to FIG. 4. In some implementations, the location of cylindrical segment 313 at the axis 314 of the force transformation mechanism 306 can save space in comparison to the counterbalance mechanism 200 of FIG. 2, in which corresponding counterbalance element 205 has a center axis that is at a different location than the axis of rotation 214 of the force transformation mechanism 206.

Cylindrical segment 313 is fixed to mechanical ground 301, e.g., to the grounded member that is coupled to rotatable member 330. In some implementations, cylindrical segment 313 is rigidly coupled to the same ground member to which force transformation mechanism 306 is rotationally coupled. In some implementations, cylindrical segment 313 and force transformation mechanism 306 can be coupled to different ground members. Tension element 320 is routed against the cylindrical surface 317 of cylindrical segment 313 and is coupled to mechanical ground 301 via cylindrical segment 313. In various implementations, tension element 320 can be wrapped around cylindrical segment 313 (or a pulley or other element in place of segment 313) by a different amount depending on the implementation, e.g., depending on the range of motion of rotating member 330.

Pulley 303 can be rotationally coupled to rotatable member 330 similarly as described for pulley 203 of FIG. 2. Pulley 303 has an axis of rotation 328 that is coaxial with a joint axis of the rotary joint that couples the rotatable member 330 to a ground or grounded member. Pulley 304 is rotationally coupled to rotatable member 330 and swings about axis 328 and pulley 303 with the rotatable member 330 as it rotates. Rotatable member 330 has mass m and a center of mass 325 that is on the opposite side of axis 328 from pulley 304. In some implementations, pulley 304 is positioned in line, along a length of the rotatable member 330, with center of mass of mass 325 and axis of rotation 328.

In operation, rotatable member 330 can rotate about axis 328. Spring 302 provides a force on tension element 308 which resists motion of pulley 304 about the axis 328 caused by rotation of rotatable member 330, thus providing a counterbalance force on rotatable member 330 that opposes gravitational force 340 on the rotatable member.

As shown in FIG. 3, an angle θ is denoted between the current orientation of pulley 304 and an orientation of the pulley 304 that would cause pulley 303, pulley 304, and cylindrical segment 313 to be aligned, e.g., their centers intersected by a single line. In FIG. 3, the three-pulley-aligned orientation is the vertical line 326. The same angle θ exists between the center of mass 325 and its stable equilibrium position along vertical line 326 (not shown).

Design parameters of the counterbalance mechanism 300 include distances between components of the mechanism 300 and/or rotatable member 330. The planar distance of the center of mass 325 to the axis of rotation 328 is L (not shown). The planar distance between axis of rotation 328 and the axis of rotation of the pulley 304 is a (not shown). The planar distance between axis of rotation 328 and the center axis 314 of the cylindrical segment 313 is b (not shown). The distance between the axis of rotation of pulley 303 and the center axis 314 of cylindrical segment 313 is d (not shown). For example, since pulley 304 rotates with rotatable member 330, distance d varies and is a function of a, b, and angle θ at which the rotatable member 330 is currently oriented. Another parameter of the counterbalance mechanism 300 is k, the spring rate (spring constant) of spring 302.

Balancing the gravity load of the rotatable member 330 can be performed by matching a product of the design parameters k, a, b, and R to the gravity load, similarly as explained above for FIG. 2 (e.g., Equation (4)). As rotating member 330 rotates, the counterbalance force applied to the rotating member is dynamically adjusted to compensate for gravity as applied during the rotation.

Counterbalance mechanism 300 also allows more design flexibility relative to conventional implementations by enabling variable parameter values of components of force transformation mechanism 306 provided between tension element 320 and spring 302. Force transformation mechanism 306 provides a mechanical transformation between the loop of tension element 320 and spring 302 similarly as described above for counterbalance mechanism 200. For example, the mechanical transformation can be a force reduction or a force amplification.

The amount of mechanical transformation is based on the drive ratio between first transform pulley 310 and second transform pulley 312, similar as described for FIG. 2. For example, the drive ratio between first transform pulley 310 and second transform pulley 312 can be R=r1/r2, where r1 is the radius of first transform pulley 310 and r2 is the radius of second transform pulley 312. This gearing effect can alternatively be achieved with other force transformation mechanisms such as a spur gear set, planetary gear set, capstan drive, etc., some examples of which are described below with respect to FIGS. 5 and 6. In the examples of FIGS. 2 and 3, the tension pulley connected to the load has a radius of r1 and the tension pulley connected to the counterbalance spring has a radius of r2. Different configurations can be used in other implementations.

To use counterbalance mechanism 300 in a conventional manner, radius r1 is set equal to radius r2 such that R=1. A particular amount of mechanical transformation can be applied to the counterbalance force from spring 302 to tension element 320 by making the radius of one of the transform pulleys 310 or 312 different than the radius of the other transform pulley 312 or 310, e.g., by making the drive ratio R be different than 1. For example, to obtain a drive amplification implementation, the drive ratio R can be made less than 1 (R<1), and tension element 320 sees greater force than tension element 308, such that the spring force from spring 302 is amplified on tension element 320 compared to the conventional implementation in which R is equal to 1. Using a drive ratio R<1 and all other components staying the same, the travel of spring 302 is greater than in the conventional implementation.

Conversely, to obtain a force reduction implementation, the drive ratio R can be made greater than 1 (R>1), and tension element 320 sees lower force than tension element 308, such that the spring force from spring 302 is reduced on tension element 320 compared to the conventional implementation in which R is equal to 1. Using a drive ratio R>1 and all other components staying the same, the travel of spring 302 is less than in the conventional implementation.

The example counterbalance mechanism 300 shown in FIG. 3 provides gear amplification, where R<1.

In some implementations, the moment generated by the counterbalance mechanism 300 on the rotating link about axis 328 can be the same Equation (3) above. Counterbalance mechanism 300 can satisfy the relationship shown in Equation (4) to match the gravity load of rotating member 330, similarly as described for FIG. 2. For example, when 0 is zero, the spring deflection of spring 302 depends on the particular mechanical advantage (e.g., drive ratio) selected for force transformation mechanism 306. Specifically, when 0 is zero, the spring deflection is as shown in Equation (5), above.

Similarly as described above for FIG. 2, a drive ratio can be selected based on particular parameter values of components used in the counterbalance mechanism 300, or parameter value(s) of components can be selected based on a particular drive ratio being used in the counterbalance mechanism 300. The extra design capability and flexibility in the counterbalance mechanism 300 allow the counterbalance mechanism 300 to be configured appropriately to constraints of a particular system or application, similarly as described above for FIG. 2.

Figure 4:
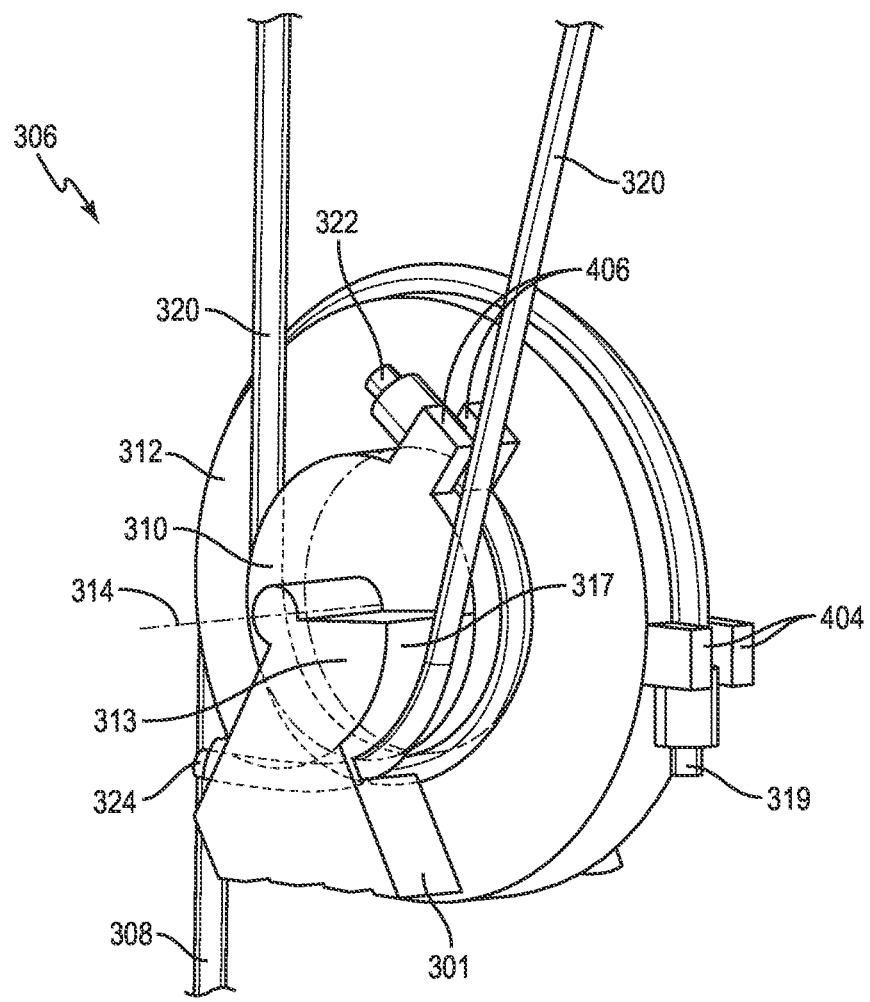
FIG. 4 is a diagrammatic illustration of an example force transformation mechanism that can be used in the counterbalance mechanism of FIG. 3, according to some implementations.

FIG. 4 is a diagrammatic illustration of an example force transformation mechanism 306 that can be used in counterbalance mechanism 300 of FIG. 3, according to some implementations. Force transformation mechanism 306 can alternatively be used in other implementations of a counterbalance mechanism.

First transform pulley 310 and second transform pulley 312 of force transformation mechanism 306 and cylindrical segment 313 are shown in FIG. 4. Tension element 308, which is connected at a first end to spring 302 in FIG. 3, is routed around second transform pulley 312 and is anchored to pulley 312 at a portion of tension element 308 near the second end 319 of tension element 308 in a termination fixture 404 that can be coupled to or part of second transform pulley 312.

Tension element 320, which is wrapped around pulleys 303 and 304 in FIG. 3, is routed around first transform pulley 310 and is anchored to pulley 310 at a portion of tension element 320 near first end 322 of tension element 320. For example, first end 322 of tension element 320 can be anchored in a termination fixture 406 that can be part of, or coupled to, first transform pulley 310.

From first transform pulley 310, tension element 320 is routed around pulleys 303 and 304 and is routed back to force transformation mechanism 306. In this example, tension element 320 is routed against circumferential surface 317 of cylindrical segment 313. In some implementations, as shown, surface 317 is located at the same distance from axis 314 as the cylindrical surface of the first transform pulley 310, such that these surfaces are aligned. In other implementations, surface 317 can be at the same distance from axis 314 as the surface of second transform pulley 312. In other implementations, surface 317 can be at a different distance from axis 314 than the surface of first transform pulley 310 or the surface of second transform pulley 312. In this example, cylindrical segment 313 is rotationally coupled to first transform pulley 310 and is rigidly coupled to mechanical ground 301. Second end 324 of tension element 320 can be anchored to cylindrical segment 313. In this example, second end 324 of tension element 320 is routed through and anchored to ground 301.

This example implementation thus provides first and second transform pulleys 310 and 312 with an axis of rotation 314 that is also a central axis of the third cylindrical segment 313 with respect to circumferential surface 317 of the segment 313. In other implementations, cylindrical segment 313 can be a cylindrical pulley having a center axis as axis 314. Other configurations can alternatively be used, e.g., locating the cylindrical segment 313 at a different location than the axis 314 of first transform pulley 310 and second transform pulley 312, or locating cylindrical segment 313 on the rotary axis of either first transform pulley 310 or second transform pulley 312 in implementations in which transform pulleys 310 and 312 have separate axes of rotation (e.g., examples similar to those described for FIGS. 5 and 6).

Figure 5:
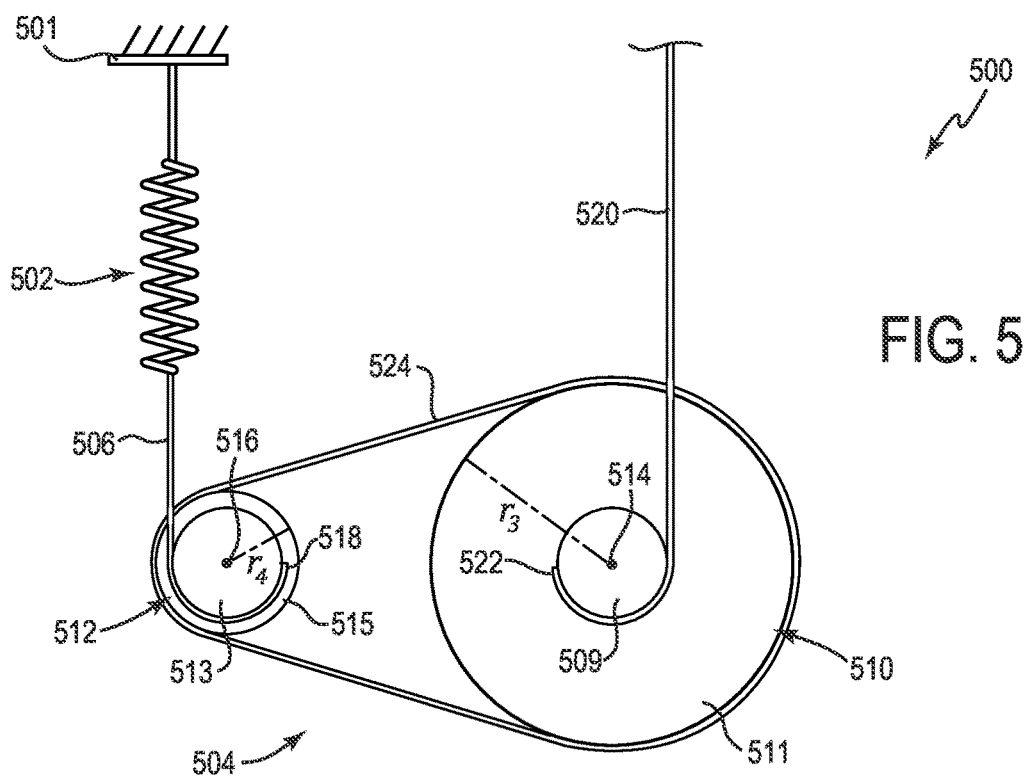
FIG. 5 is a diagrammatic illustration of a portion of another example counterbalance mechanism including one or more features of the present disclosure, according to some implementations.

FIG. 5 is a diagrammatic illustration of a portion 500 of another example counterbalance mechanism including one or more features of the present disclosure, according to some implementations. Counterbalance mechanism portion 500 can be used to provide counterbalance forces to a load, e.g., a rotating member of a mechanical arm, to counter gravitational forces on the load, similarly as described above for FIGS. 2 and 3. FIG. 5 shows an example of a force transformation mechanism that includes a belt and pulley mechanism.

In this example, the counterbalance mechanism includes a spring 502 and a force transformation mechanism 504. Spring 502 is coupled to a mechanical ground 501 at a first end of the spring. A second end of the spring is coupled to a first end of a tension element 506. Spring 502 can provide a spring force on tension element 506 similarly as described in implementations above.

In the implementation of FIG. 5, force transformation mechanism 504 modifies the magnitudes of forces provided by spring 502. Force transformation mechanism 504 includes a first transform element 510, a second transform element 512, and a belt 524. First transform element 510 rotates about a rotational axis 514 and second transform element 512 rotates about a rotational axis 516. In some examples, first transform element 510 and second transform element 512 can be rotationally coupled to mechanical ground 501 similarly as corresponding elements of FIGS. 2 and 3.

First transform element 510 can include an input/output pulley 509 and a belt pulley 511 which are rigidly coupled to each other and rotate in unison about axis 514. In some examples, first transform element 510 can be manufactured as multiple separate parts (e.g., separate pulleys 509 and 511) that are assembled to form element 510, or element 510 can be manufactured as a single, unitary part that includes pulleys 509 and 511 (e.g., machined from a single piece of material). Second transform element 512 can include an input/output pulley 513 and a belt pulley 515 which are rigidly coupled to each other and rotate in unison about axis 516. In some examples, second transform element 512 can be manufactured as multiple separate parts (e.g., separate pulleys 513 and 515) that are assembled to form element 512, or element 512 can be manufactured as a single, unitary part that includes pulleys 513 and 515 (e.g., machined from a single piece of material).

Tension element 506 is coupled to second transform element 512. For example, tension element 506 wraps at least partially around input/output pulley 513 and terminates at input/output pulley 513, where it is anchored at a second end 518 of tension element 506. In the example shown, tension element 506 is wrapped in a first direction (e.g., clockwise as shown in FIG. 5) around input/output pulley 513 from second end 518 of tension element 506. In various implementations, tension element 506 can be wrapped around input/output pulley 513 by a different amount depending on the implementation, e.g., depending on the range of motion of the load. In some implementations, other features or surfaces can be provided on second transform element 512 around which to wrap tension element 506.

A tension element 520 is coupled to first transform element 510. For example, tension element 520 wraps at least partially around input/output pulley 509 and terminates at input/output pulley 509, where it is anchored at a first end 522 of tension element 520. In this example, input/output pulley 509 has the same radius as input/output pulley 513. In the example shown, tension element 520 is wrapped in a second direction (e.g., counterclockwise as shown in FIG. 5) around input/output pulley 509 from first end 522 of tension element 520, and the second direction is opposite to the first direction of tension element 506 around input/output pulley 513. In various implementations, tension element 520 can be wrapped around input/output pulley 509 by a different amount depending on the implementation, e.g., depending on the range of motion of the load. In some implementations, other features or surfaces can be provided on first transform element 510 around which to wrap tension element 520.

Tension element 520 is routed from input/output pulley 509 to wrap at least partially around one or more other pulleys (not shown in FIG. 5) where it can terminate at a second end. For example, tension element 520 can wrap around two counterbalance pulleys in a configuration similar to the pulleys 203 and 204 and counterbalance element 205 of FIG. 2, and pulleys 203 and 204 are rotationally coupled to a rotating member similarly as described for FIG. 2. In some implementations, a counterbalance element can be coupled to one of input/output pulley 509 or input/output pulley 513, similarly to cylindrical segment 313 coupled to second transform pulley 312 of FIG. 3.

First transform element 510 is coupled to second transform element 512 by belt 524. In this example, belt 524 is a tension member formed in a continuous loop that wraps around both belt pulley 511 of first transform element 510 and belt pulley 515 of second transform element 512. In various implementations, as shown, the radius of belt pulley 511 can be larger than, smaller than, or equal than the radius of input/output pulley 509 of first transform element 510. In various implementations, the radius of belt pulley 515 can be larger than, smaller than, or equal to the radius of input/output pulley 513 of second transform element 512.

Belt 524 links the rotation of first transform element 510 and second transform element 512 about their axes 514 and 516, respectively, and these rotations of elements 510 and 512 are in the same direction. Thus, if force transmitted via tension element 520 causes first transform element 510 to rotate about axis 514 in a counterclockwise direction in the viewpoint shown in FIG. 5, belt 524 transmits this rotation to second transform element 512 and causes second transform element 512 to rotate about axis 516 in the same direction, which causes the length of spring 502 to increase (stretch). Similarly, rotation of second transform element 512 in a clockwise direction by tension element 506 (in the viewpoint of FIG. 5) causes rotation of first transform element 510 in the same direction, which causes force on tension element 520 toward the force transformation mechanism.

Belt 524 can be made of any suitable material (e.g., elastic material, metal, etc.), and in some implementations can include features (e.g., cogs or teeth) that enable the belt to contact corresponding features in the belt pulley 511 of first transform element 510 and/or corresponding features in the belt pulley 515 of second transform element 512 to reduce slippage of the belt on these elements 510 and 512. In some implementations, belt 524 can be a chain, cable, or other tension member. In some implementations, belt 524 can include two or more belts and/or can have ends terminated respectively at the transform elements 510 and 512.

Force transformation mechanism 504 provides a mechanical transformation between tension element 520 and spring 502, similarly to the force transformation mechanisms of FIGS. 2 and 3. The mechanical transformation can be a force reduction or a force amplification. The amount of mechanical transformation is based on the drive ratio between first transform element 510 and second transform element 512.

The radii of first transform element 510 (indicated here by the radius of belt pulley 511) and second transform element 512 (indicated here by the radius of belt pulley 515) determines the drive ratio. For example, first transform element 510 can be selected to have a radius r3 and second transform element 512 can be selected to have a radius r4. If r3=r4, there is no mechanical transformation and the counterbalance mechanism can operate similarly to that of FIG. 1. If r3 is different than r4, mechanical transformation is applied. For example, the drive ratio between first transform element 510 and second transform element 512 can be R=r4/r3. To obtain a force amplification implementation, the drive ratio R can be made less than 1 (R<1), such that the spring force from spring 502 is amplified on tension element 520 compared to the conventional implementation in which R is equal to 1. Using a drive ratio R<1 and all other components and configuration staying the same, the travel of spring 502 is greater than in the conventional implementation.

Conversely, to obtain a force reduction implementation, the drive ratio R can be made greater than 1 (R>1), such that the spring force from spring 502 is reduced on tension element 520 compared to the conventional implementation in which R is equal to 1. Using a drive ratio R>1 and all other components and configuration staying the same, the travel of spring 502 is less than in the conventional implementation.

For example, the counterbalance mechanism including portion 500 as shown in FIG. 5 provides force amplification, where R<1 similarly as in FIG. 3.

In some implementations, Equations (3), (4), and (5) above can be used to match the gravity load of the load of the counterbalance mechanism, similarly as described for FIG. 2. A drive ratio for force transformation mechanism 504 can be selected based on particular parameter values of components used in the counterbalance mechanism, or parameter value(s) of components can be selected based on a particular drive ratio being used in the counterbalance mechanism, similarly as described above for FIGS. 2 and 3.

Figure 6:
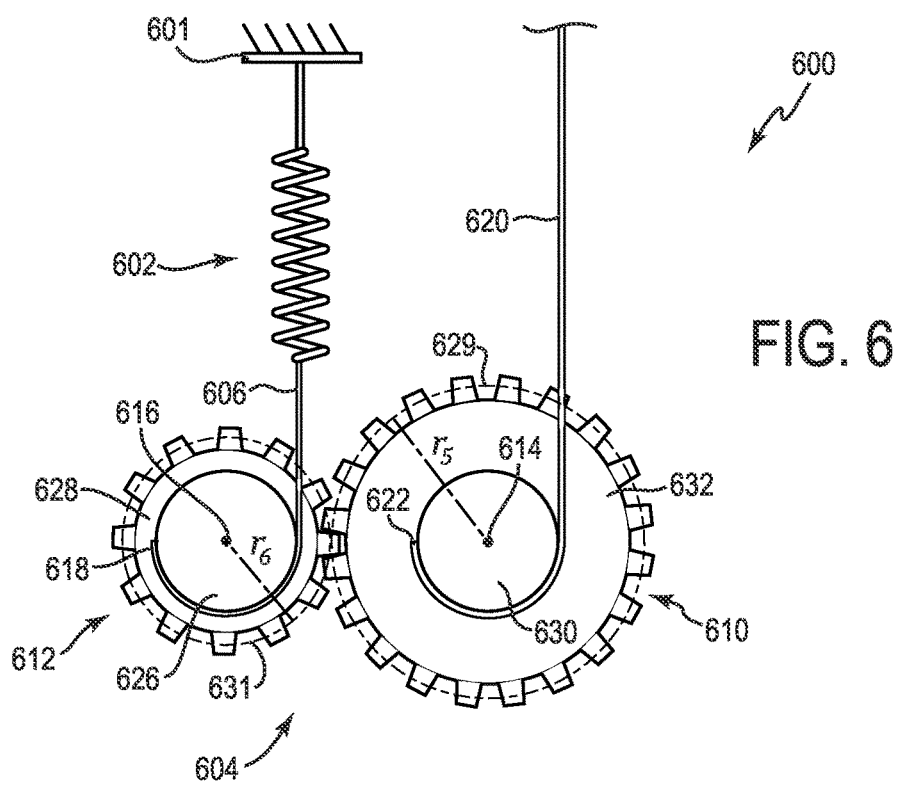
FIG. 6 is a diagrammatic illustrations of a portion of another example counterbalance mechanism including one or more features of the present disclosure, according to some implementations.

FIG. 6 is a diagrammatic illustration of a portion 600 of another example counterbalance mechanism including one or more features of the present disclosure, according to some implementations. Counterbalance mechanism portion 600 can be used to provide counterbalance forces to a load, e.g., a rotating member of a mechanical arm, to counter gravitational forces on the load, similarly as described above for FIGS. 2, 3, and 5. FIG. 6 shows an example of a force transformation mechanism that includes multiple spur gears.

In this example, the counterbalance mechanism includes a spring 602 and a force transformation mechanism 604. Spring 602 is coupled to a mechanical ground 601 at a first end of the spring. A second end of the spring is coupled to a first end of a tension element 606. Spring 602 can provide a spring force on tension element 606.

In the implementation of FIG. 6, force transformation mechanism 604 modifies the magnitudes of forces provided by spring 602. Force transformation mechanism 604 includes a first transform element 610 and a second transform element 612. First transform element 610 rotates about a rotational axis 614 and second transform element 612 rotates about a rotational axis 616. In some examples, first transform element 610 and second transform element 612 can be rotationally coupled to mechanical ground 601 similarly as corresponding transform pulleys of FIGS. 2, 3, and 5.

First transform element 610 can include an inner pulley 630 and an outer gear 632 which are rigidly coupled to each other and rotate in unison about axis 614. In some examples, first transform element 610 can be manufactured as multiple separate parts (e.g., separate pulley 630 and gear 632) that are assembled to form element 610, or element 610 can be manufactured as a single, unitary part that includes pulley 630 and gear 632 (e.g., machined from a single piece of material). Second transform element 612 can include an inner pulley 626 and an outer gear 628 which are rigidly coupled to each other and rotate in unison about axis 616. In some examples, second transform element 612 can be manufactured as multiple separate parts (e.g., separate pulley 626 and gear 628) that are assembled to form element 612, or element 612 can be manufactured as a single, unitary part that includes pulley 626 and gear 628 (e.g., machined from a single piece of material).

Tension element 606 is coupled to second transform element 612 at a second end 618. Tension element 606 is wrapped at least partially around the inner pulley 626 of second transform element 612 and is anchored to second transform element 612 at second end 618 of tension element 606. In the example shown, tension element 606 is wrapped in a first direction (e.g., counterclockwise as shown in FIG. 6) around inner pulley 626 from the second end 618 of tension element 606. In various implementations, tension element 606 can be wrapped around inner pulley 626 by a different amount depending on the implementation, e.g., depending on the range of motion of the load. In some implementations, other features or surfaces can be provided on second transform element 612 around which to wrap tension element 606.

A tension element 620 is coupled to inner pulley 630 at a first end 622, where it is anchored to first transform element 610. Tension element 620 is wrapped at least partially around the inner pulley 630. In the example shown, tension element 620 is wrapped in a second direction (e.g., counterclockwise as shown in FIG. 6) around inner pulley 630 from second end 622 of tension element 620, and the second direction is the same direction as the first direction of tension element 606 around second transform element 612. In various implementations, tension element 620 can be wrapped around inner pulley 630 by a different amount depending on the implementation, e.g., depending on the range of motion of the load. In some implementations, other features or surfaces can be provided on first transform element 610 around which to wrap tension element 620.

Tension element 620 is routed from first transform element 610 to wrap at least partially around multiple other pulleys (not shown in FIG. 6) where it can terminate at a second end. For example, tension element 620 can wrap around two counterbalance pulleys in a configuration similar to the pulleys 203 and 204 and a counterbalance element 205 of FIG. 2, and pulleys 203 and 204 are rotationally coupled to a rotating member similarly as described for FIG. 2. In some implementations, a counterbalance element can be coupled to one of first transform element 610 or second transform element 612, similarly to cylindrical segment 313 coupled to second transform pulley 312 of FIG. 3.

First transform element 610 is engaged with second transform element 612 via the gear teeth of outer gear 632 and the gear teeth of outer gear 628. The engaged gear teeth link the rotation of first transform element 610 and second transform element 612 about their axes 614 and 616, respectively, and these rotations of transform elements 610 and 612 are in opposite directions. Thus, if force transmitted via tension element 620 causes first transform element 610 to rotate about axis 614 in a counterclockwise direction in the viewpoint shown in FIG. 6, the engaged gear teeth transmit this rotation to second transform element 612 and cause second transform element 612 to rotate about axis 616 in the opposite (clockwise) direction, which causes the length of spring 602 to increase (stretch). Similarly, rotation of second transform element 612 in a counterclockwise direction by tension element 606 (in the viewpoint of FIG. 6) causes rotation of first transform element 610 in a clockwise direction, which causes force on tension element 620 toward the force transformation mechanism 604.

Any suitable amount of gear teeth can be used for first transform element 612 and second transform element 614. In some implementations, other features or mechanisms can be used to engage the circumferential surfaces of first and second transform elements 610 and 612 to provide linked rotation as described.

Force transformation mechanism 604 provides a mechanical transformation between tension element 620 and spring 602, similarly to the force transformation mechanisms of FIGS. 2 and 3. The mechanical transformation can be a force reduction or a force amplification. The amount of mechanical transformation is based on the drive ratio between first transform element 610 and second transform element 612.

The radii of first transform element 610 (indicated here by a pitch circle 629 for outer gear 632) and second transform element 612 (indicated here by a pitch circle 631 for outer gear 628) can be used to determine the drive ratio. For example, first transform element 610 can be selected to have a pitch circle radius r5 and second transform element 612 can be selected to have a pitch circle radius r6. If r5=r6, there is no mechanical transformation and the counterbalance mechanism can operate similarly to that of FIG. 1. If r5 is different than r6, mechanical transformation is applied. For example, the drive ratio between first transform element 610 and second transform element 612 can be R=r6/r5. To obtain a force amplification implementation, the drive ratio R can be made less than 1 (R<1), such that the spring force from spring 602 is amplified on tension element 620 compared to the conventional implementation in which R is equal to 1. Using a drive ratio R<1 and all other components and configuration staying the same, the travel of spring 602 is greater than in the conventional implementation.

Conversely, to obtain a force reduction implementation, the drive ratio R can be made greater than 1 (R>1), such that the spring force from spring 602 is reduced on tension element 620 compared to the conventional implementation in which R is equal to 1. Using a drive ratio R>1 and all other components and configuration staying the same, the travel of spring 602 is less than in the conventional implementation.

For example, the counterbalance mechanism including portion 600 shown in FIG. 6 provides force amplification, where R<1 similarly as in FIG. 3.

In some implementations, Equations (3), (4), and (5) above can be used to match the gravity load of the load of the counterbalance mechanism, similarly as described for FIG. 2. A drive ratio for force transformation mechanism 604 can be selected based on particular parameter values of components used in the counterbalance mechanism, or parameter value(s) of components can be selected based on a particular drive ratio being used in the counterbalance mechanism, similarly as described above for FIGS. 2 and 3.

In some implementations, other types of force transformation mechanisms can be used instead of the force transformation mechanisms 206, 306, 504, and 604 shown in FIGS. 2-6. For example, a capstan drive mechanism can be used. In some examples, first transform element 510 or first transform element 610 is replaced by a capstan drum and second transform element 512 or second transform element 612 is replaced by a capstan pulley (or vice-versa), and the capstan pulley is coupled to the capstan drum by a tension element.

For example, a first end of the capstan tension element can be attached to a first end of the capstan drum, and the tension element is routed along the side surface of the capstan drum, wrapped around the capstan pulley, and routed along the side surface of the capstan drum to a second end of the drum where the second end of the tension element is attached. In operation, rotation of the capstan pulley (e.g., caused by tension element 506/606 or 520/620) is transmitted through the tension element, via winding and unwinding of the tension element around the capstan pulley, to cause rotation of the capstan drum. Similarly, rotation of the capstan drum (e.g., caused by tension element 506/606 or 520/620) is transmitted through the tension element to cause rotation of the capstan pulley.

The functional blocks, operations, features, methods, devices, and systems described in the present disclosure may be integrated or divided into different combinations of systems, devices, and functional blocks.

Although the present implementations have been described in accordance with the examples shown, there can be variations to the implementations and those variations are within the spirit and scope of the present disclosure. Accordingly, many modifications may be made without departing from the spirit and scope of the appended claims.

What is claimed is:

1. A counterbalance apparatus comprising:
a spring;
a first tension element;
a second tension element;
a force transformation mechanism coupled to the spring by the first tension element and coupled to the second tension element, the force transformation mechanism including a first radius and a second radius that is different than the first radius, the force transformation mechanism rotationally coupled to a mechanical ground; and
a plurality of counterbalance pulleys coupled to the second tension element;
wherein:
at least one of the plurality of counterbalance pulleys is coupled to a load that is moveable with reference to the mechanical ground;
the load includes a first member rotationally coupled to a second member at a rotary joint having a rotary joint axis, the second member being coupled to the mechanical ground, and the first member being rotatable with respect to the second member about the rotary joint axis of the rotary joint;
a force provided by the spring is modified in magnitude by the force transformation mechanism and is applied to the load via the second tension element; and
the modification of the force is based on a drive ratio of the first radius and the second radius of the force transformation mechanism.

2. The counterbalance apparatus of claim 1, wherein:
the force transformation mechanism includes a first transform pulley having the first radius and a second transform pulley having the second radius; and
the first transform pulley is rigidly coupled to the second transform pulley.

3. The counterbalance apparatus of claim 2, wherein:
the first tension element is coupled to the first transform pulley; and
the second tension element is coupled to the second transform pulley.

4. The counterbalance apparatus of claim 2, wherein:
the first transform pulley and the second transform pulley are rotatable about a rotational axis, and
the counterbalance pulleys are rotatable about center axes that are different than the rotational axis of the first transform pulley and the second transform pulley.

5. The counterbalance apparatus of claim 1, wherein:
the force of the spring is modified by the force transformation mechanism such that a gravity force on the load is balanced.

6. The counterbalance apparatus of claim 1, wherein:
the drive ratio is selected based on a particular spring rate of the spring; and
a magnitude of the force provided by the spring to the load is configured based at least on the particular spring rate and the drive ratio.

7. The counterbalance apparatus of claim 1, wherein:
the drive ratio is selected based on a specified extension length of the spring; and a travel distance of the spring during operation of the counterbalance apparatus is configured based at least on the specified extension length of the spring and the drive ratio.

8. The counterbalance apparatus of claim 1, wherein:
the plurality of counterbalance pulleys include a first counterbalance pulley and a second counterbalance pulley; and
the second tension element is wrapped at least partially around the first counterbalance pulley and at least partially around the second counterbalance pulley.

9. The counterbalance apparatus of claim 1, wherein:
the plurality of counterbalance pulleys includes a first counterbalance pulley and a second counterbalance pulley having a rotary axis;
the first counterbalance pulley is rotationally coupled to the first member of the load at the rotary joint of the load and is rotatable about the rotary joint axis of the rotary joint of the load;
the second counterbalance pulley is rotationally coupled to the first member of the load and is rotatable about the rotary axis of the second counterbalance pulley;
the rotary axis of the second counterbalance pulley is different than the rotary joint axis of the rotary joint of the load; and
the rotary axis of the second counterbalance pulley is in line, along a length of the first member, with the rotary joint axis of the rotary joint of the load and with a center of mass of the first member.

10. The counterbalance apparatus of claim 1, wherein:
the counterbalance apparatus further includes a counterbalance element coupled to a mechanical ground;
the second tension element includes a first end portion coupled to the force transformation mechanism; and
the second tension element includes a second end portion coupled to the counterbalance element.

11. The counterbalance apparatus of claim 10, wherein:
the counterbalance element includes a cylindrical segment rotationally coupled to the force transformation mechanism and rigidly coupled to the mechanical ground.

12. The counterbalance apparatus of claim 1, wherein:
the plurality of counterbalance pulleys includes a first counterbalance pulley and a second counterbalance pulley;
the counterbalance apparatus includes a counterbalance element;
the second tension element includes a first end portion coupled to the force transformation mechanism;
the second tension element includes a second end portion coupled to the counterbalance element; and
the second tension element is at least partially wrapped around the first counterbalance pulley, at least partially wrapped around the second counterbalance pulley, and at least partially wrapped around the counterbalance element.

13. The counterbalance apparatus of claim 1, wherein:
the counterbalance apparatus is embodied in one of: a user control system of a teleoperated surgical system, or a manipulator device of a teleoperated surgical system.

14. An apparatus comprising:
a mechanical arm including a rotary joint, a first member, and a second member rotationally coupled to the first member at the rotary joint;
a spring coupled to the second member;
a first tension element coupled to the spring;
a force transformation mechanism coupled to the second member, and coupled to the first tension element, and rotationally coupled to a mechanical ground;
a second tension element coupled to the force transformation mechanism; and
a plurality of counterbalance pulleys coupled to the mechanical arm;
wherein:
at least one of the plurality of counterbalance pulleys is coupled to the first member of the mechanical arm;
the second tension element is wrapped at least partially around at least one counterbalance pulley of the plurality of counterbalance pulleys;
the force transformation mechanism includes at least one rotatable element having a drive ratio between a first radius and a second radius of the at least one rotatable element, wherein the first radius is different than the second radius;
the force transformation mechanism is configured to mechanically transform a force provided by the spring and transmitted via the second tension element to the first member; and
the mechanical transformation of the force is based on the drive ratio of the at least one rotatable element of the force transformation mechanism.

15. The apparatus of claim 14 wherein:
the force provided by the spring is modified by the force transformation mechanism such that a gravity force on the second member of the mechanical arm is balanced; and
the drive ratio determines the mechanical transformation to be a force reduction or a force amplification based on a relative size of the first radius and the second radius of the at least one rotatable element.

16. The apparatus of claim 14, wherein:
the at least one rotatable element of the force transformation mechanism includes a first element having the first radius and a second element having the second radius;
the drive ratio of the at least one rotatable element of the force transformation mechanism is based on a ratio between the first radius and the second radius;
the first tension element is coupled to the first element of the force transformation mechanism; and
the second tension element is coupled to the second element of the force transformation mechanism.

17. The apparatus of claim 16, wherein:
the first element of the force transformation mechanism is a first transform pulley;
the second element of the force transformation mechanism is a second transform pulley;
the first transform pulley and the second transform pulley have the same axis of rotation; and
the first transform pulley is rigidly coupled to the second transform pulley.

18. The apparatus of claim 14, wherein:
the second member of the mechanical arm is coupled to the mechanical ground;
the plurality of counterbalance pulleys includes a first counterbalance pulley and a second counterbalance pulley;
the first counterbalance pulley is coupled to the mechanical arm at the rotary joint of the mechanical arm;
the second counterbalance pulley is coupled to the second member of the mechanical arm;
the rotary joint of the mechanical arm has an axis of rotation; and the first counterbalance pulley has an axis of rotation aligned with the axis of rotation of the rotary joint of the mechanical arm.

19. The apparatus of claim 18, wherein:

the apparatus further includes a counterbalance element that includes a cylindrical segment rotationally coupled to the force transformation mechanism and rigidly coupled to the mechanical ground;

the second tension element includes a first end portion coupled to the force transformation mechanism; and the second tension element includes a second end portion coupled to the counterbalance element.

20. An apparatus comprising:

a mechanical arm including a rotary joint, a first member, and a second member rotationally coupled to the first member at the rotary joint;

a spring coupled to the second member;

a first tension element coupled to the spring;

a force transformation mechanism coupled to the second member and to the first tension element and rotationally coupled to a mechanical ground;

a second tension element coupled to the force transformation mechanism;

a plurality of counterbalance pulleys coupled to the mechanical arm; and a counterbalance element coupled to the mechanical ground, the counterbalance element including a cylindrical segment rotationally coupled to the force transformation mechanism and rigidly coupled to the mechanical ground;

wherein:

at least one of the plurality of counterbalance pulleys is coupled to the first member of the mechanical arm;

the second tension element is wrapped at least partially around at least one counterbalance pulley of the plurality of counterbalance pulleys;

the force transformation mechanism includes at least one rotatable element, the at least one rotatable element including a first radius and a second radius and having a drive ratio of the first radius and the second radius;

the force transformation mechanism is configured to mechanically transform a force provided by the spring and transmitted via the second tension element to the first member; and the mechanical transformation of the force is based on the drive ratio of the at least one rotatable element of the force transformation mechanism.

* * * * *